United States Patent [19]
Hellberg

[11] Patent Number: 6,096,783
[45] Date of Patent: Aug. 1, 2000

[54] CYCLOBUTANE PROSTAGLANDIN ANALOGUES AS OCULAR HYPOTENSIVE AGENTS

[75] Inventor: Mark R. Hellberg, Arlington, Tex.

[73] Assignee: Alcon Laboratories, Inc., Fort Worth, Tex.

[21] Appl. No.: 09/212,372

[22] Filed: Dec. 15, 1998

Related U.S. Application Data

[60] Provisional application No. 60/068,486, Dec. 22, 1997.

[51] Int. Cl.$^7$ ...................... C07C 69/608; C07C 69/616; A61K 31/215; A61K 31/216

[52] U.S. Cl. .......................... 514/530; 514/529; 514/530; 514/534; 514/543; 560/56; 560/60; 560/62; 560/118

[58] Field of Search ..................................... 514/530, 534, 514/543, 529; 560/118, 56, 60, 62

[56] References Cited

U.S. PATENT DOCUMENTS

| | | |
|---|---|---|
| 3,772,350 | 11/1973 | Pike et al. |
| 4,599,353 | 7/1986 | Bito. |
| 5,001,153 | 3/1991 | Ueno et al. |
| 5,093,329 | 3/1992 | Woodward. |
| 5,321,128 | 6/1994 | Stjernschantz et al. |

FOREIGN PATENT DOCUMENTS

| | | |
|---|---|---|
| 330511 A2 | 8/1989 | European Pat. Off. |
| 561073 A1 | 9/1993 | European Pat. Off. |
| 2646855 | 10/1976 | Germany. |
| 2705675 | 2/1977 | Germany. |
| WO 92/08465 | 5/1992 | WIPO. |

OTHER PUBLICATIONS

Alm, The Potential of Prostaglandin Derivatives in Glaucoma Therapy, *Current Opinion in Ophthalmology*, 4(11):44–50 (1993).

Depres et al., Synthesis of Ring Modified Prostaglandins, *Tetrahedron*, 37(3): 621–628 (1981).

Flach, Eliason, Topical Prostaglandin $E_2$ Effects on Normal Human Intraocular Pressure *Journal of Ocular Pharmacology*, 4(1):13–17 (1988).

Giuffre, The Effects of Prostaglandin $F_{2\alpha}$ the Human Eye, *Graefe's Arch Clin Exp Ophthalmol*, 222:139–141 (1985).

Greene et al., Total Synthesis of 11–Nor Prostaglandins, *Tetrahedron Letters*, 41:3755–3758 (1976).

Guzmán, et al., Synthesis of Cyclobutano Prostaglandins, *Chemistry and Industry*, 20:884–885 (Oct. 1975).

Ichikawa, Sugimoto, Negishi, Molecular aspects of the structures and functions of the prostaglandin E receptors, *J. Lipid Mediators Cell Signalling*, 14:83–87 (1996).

Kerstetter et al., Prostaglandin $F_{2\alpha}$–1–Isopropylester Lowers Intraocular Pressure Without Decreasing Aqueous Humor Flow, *American Journal of Ophthalmology* 105:30–34 (1988).

Nakajima et al. Effects of Prostaglandin $D_2$ and its analogue, BW245C, on Intraocular Pressure in Humans, *Graefe's Archive Ophthalmology*, 229:411–413 (1991).

Reuschling et al., Synthese von Cyclobutanprostaglandinen, *Tetrahedron Letters*, 1:17–18 (1977).

Thierauch et al., Prostaglandins and their Receptors: II. Receptor Structure and Signal Transduction, *Journal of Hypertension*, 12:1–5 (1994).

Waterbury, et al., $EP_3$ but not $EP_2$ FP or TP Prostanoid–Receptor Stimulation May Reduce Intraocular Pressure, *Investigative Ophthalmology and Visual Science*, 31(12):2560–2567 (Dec. 1990).

Woodward et al., Prostaglandin $F_{2\alpha}$ effects on intraocular pressure negatively correlate with FP–Receptor Stimulation *Investigative Ophthal & Visual Sci* 30(8):1838–1842 (Aug. 1989).

Woodward, et al., Intraocular pressure effects of selective prostanoid receptor agonists involve different receptor subtypes according to radioligand binding studies, *Journal of Lipid Mediators*, 6:545–553 (1993).

Woodward, et al., Molecular Characterization and Ocular Hypotensive Properties of the Prostanoid EP2 Receptor *Journal of Ocular Pharmacology and Therapeutics*, 11(3):447–454 (1995).

*Primary Examiner*—Robert Gerstl
*Attorney, Agent, or Firm*—Barry L. Copeland

[57] ABSTRACT

Cyclobutane analogs of $PGF_{2\alpha}$, $PGD_2$, and $PGE_2$ and methods of their use in treating glaucoma and ocular hypertension are disclosed.

25 Claims, No Drawings

CYCLOBUTANE PROSTAGLANDIN ANALOGUES AS OCULAR HYPOTENSIVE AGENTS

This application claims benefit of Provisional Appl. Ser. No. 60/068,486 filed Dec. 22, 1997.

BACKGROUND OF THE INVENTION

The present invention relates to novel compounds and methods for the treatment of glaucoma and ocular hypertension. In particular, the present invention relates to the use of certain cyclobutane analogs of D, E, and F series prostaglandins to treat glaucoma and ocular hypertension.

Glaucoma is a progressive disease which leads to optic nerve damage and, ultimately, total loss of vision. The causes of this disease have been the subject of extensive studies for many years, but are still not fully understood. The principal symptom of and/or risk factor for the disease is elevated intraocular pressure or ocular hypertension due to excess aqueous humor in the anterior chamber of the eye.

The causes of aqueous humor accumulation in the anterior chamber are not fully understood. It is known that elevated intraocular pressure ("IOP") can be at least partially controlled by administering drugs which either reduce the production of aqueous humor within the eye, such as beta-blockers and carbonic anhydrase inhibitors, or increase the outflow of aqueous humor from the eye, such as miotics and sympathomimetics.

Most types of drugs conventionally used to treat glaucoma have potentially serious side effects. Miotics such as pilocarpine can cause blurring of vision and other visual side effects, which may lead either to decreased patient compliance or to termination of therapy. Systemically administered carbonic anhydrase inhibitors can also cause serious side effects such as nausea, dyspepsia, fatigue, and metabolic acidosis, which side effects can affect patient compliance and/or necessitate the termination of treatment. Another type of drug, beta-blockers, have increasingly become associated with serious pulmonary side effects attributable to their effects on beta-2 receptors in pulmonary tissue. Sympathomimetics, on the other hand, may cause tachycardia, arrhythmia and hypertension. Recently, certain prostaglandins and prostaglandin derivatives have been described in the art as being useful in reducing intraocular pressure. Typically, however, prostaglandin therapy for the treatment of elevated intraocular pressure is attended by undesirable side-effects, such as irritation and hyperemia of varying severity and duration. There is therefore a continuing need for therapies which control elevated intraocular pressure associated with glaucoma without the degree of undesirable side-effects attendant to most conventional therapies.

Prostaglandins are metabolite derivatives of arachidonic acid. Arachidonic acid in the body is converted to prostaglandin $G_2$, which is subsequently converted to prostaglandin $H_2$. Other naturally occurring prostaglandins are derivatives of prostaglandin $H_2$. A number of different types of prostaglandins have been discovered including A, B, D, E, F, G, I and J-Series prostaglandins (EP 0 561 073 A1). A number of the naturally occurring prostaglandins, including prostaglandins of the F series (such as $PGF_{2\alpha}$), the E series (such as $PGE_2$) and the D series (such as $PGD_2$) are known to lower IOP after topical ocular instillation, but can cause marked inflammation as evidenced by conjunctival edema or other untoward effects such as conjunctival hyperemia.

All of the natural prostaglandins known to reduce intraocular pressure, including prostaglandins of the F series (such as $PGF_{2\alpha}$), the E series (such as $PGE_2$) and the D series (such as $PGD_2$), have a core cyclopentane ring with alpha and omega chains attached at C-8 and C-12 respectively, as indicated in the following structures:

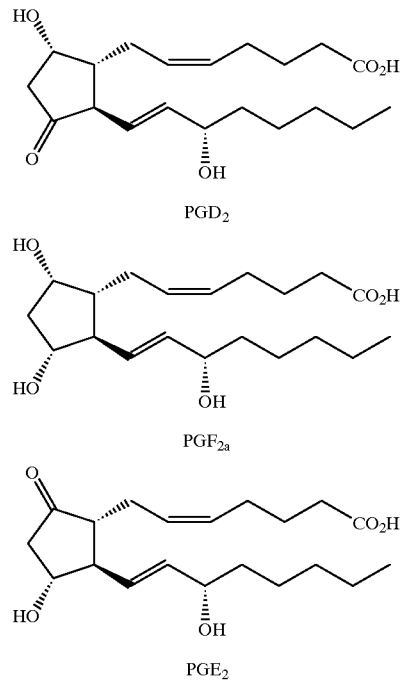

$PGD_2$ $PGF_{2a}$ $PGE_2$

Currently, the relationship between prostaglandin receptor activation and IOP lowering effects is not well understood. Various publications have reported that $PGD_2$ receptor activation leads to second messenger activation and in particular, to the stimulation of adenylate cyclase and resultant increases in cAMP levels (Thierauch, *Prostaglandins and their Receptors: II. Receptor Structure and Signal Transduction, Journal of Hypertension*, 12:1–5 (1994). Some believe that $PGF_{2\alpha}$ receptor activation, on the other hand, leads to increased outflow of aqueous humor. Regardless of the mechanism, both $PGD_2$ and $PGF_{2\alpha}$ (and certain of its analogs) have been shown to lower IOP. See (for $PGD_2$) Nakajima, *Effects of Prostaglandin $D_2$ and its analogue, BW245C, on Intraocular Pressure in Humans, Graefe's Archive Clinical Experimental Ophthalmology*, 229:411–413 (1991); and (for $PGF_{2\alpha}$), Giuffre, *The Effects of Prostaglandin $F_{2\alpha}$ on the Human Eye, Graefe's Archive Ophthalmology*, 222:139–141 (1985); and Kerstetter et al., *Prostaglandin $F_{2\alpha}$-1-Isopropylester Lowers Intraocular Pressure Without Decreasing Aqueous Humor Flow, American Journal of Ophthalmology*, 105:30–34 (1988).

Synthetic analogs of both the $PGD_2$ and $PGF_{2\alpha}$ types have been pursued in the art Nakajima, *Effects of Prostaglandin $D_2$ and its analogue, BW245C, on Intraocular Pressure in Humans*, (*Graefe's Archive Ophthalmology*, 229:411–413 (1991)). Although both types of molecules lower IOP, they have also been associated with undesirable side effects resulting from topical ophthalmic dosing. Such effects have included, among others, an initial increase in IOP and conjunctival hyperemia, (Alm, *The Potential of Prostaglandin Derivatives in Glaucoma Therapy, Current Opinion in Ophthalmology*, 4(11):44–50 (1993)).

The relationship between EP receptor activation and IOP lowering effects is also the subject of some debate. There are currently four recognized subtypes of the EP receptor: $EP_1$, EP$_2$, EP$_3$, and EP$_4$ (Ichikawa, Sugimoto, Negishi, *Molecular aspects of the structures and functions of the prostaglandin E receptors, J. Lipid Mediators Cell Signaling,* 14:83–87 (1996)). It is known in the art that IOP may be lowered by ligands capable of EP$_2$ receptor activation, such as PGE$_2$ and certain of its synthetic analogs (Fallach, Eliason, *Topical Prostaglandin E$_2$ Effects on Normal Human Intraocular Pressure Journal of Ocular Pharmacology,* 4(1):13–18 (1988)). Woodward, et al., *Molecular Characterization and Ocular Hypotensive Properties of the Prostaglandin EP2 Receptor, Journal of Ocular Pharmacology and Therapeutics,* 11(3):447–454 (1995)), or EP$_3$ receptor activation (Woodward, et al., *Intraocular pressure effects of selective prostanoid receptor agonists involve different receptor subtypes according to radioligand binding studies, Journal of Lipid Mediators,* 6:545–553 (1993)); Waterbury, et al., *EP$_3$ but not EP$_2$ FP or TP Prostanoid-Receptor Stimulation May Reduce Intraocular Pressure, Investigative Ophthalmology and Visual Science,* 31(12):2560–2567 (1990)). However, some of these molecules have also been associated with undesirable side effects resulting from topical ophthalmic dosing, including an initial increase in IOP, photophobia, and eye ache (see, for example, Flach, Eliason, *Topical Prostaglandin E$_2$ Effects on Normal Human Intraocular Pressure, Journal of Ocular Pharmacology,* 4(1):13–18 (1988)).

A number of synthetic prostaglandins have been observed to lower intraocular pressure, but such compounds also produce the aforementioned side effects in varying degrees which greatly limit their clinical utility. Based on the foregoing, a need exists for the development of molecules that may activate key prostaglandin receptors, yielding a more efficacious lowering of IOP, while exhibiting fewer or reduced side effects.

Attempts have been made by Stjernschantz et al. (U.S. Pat. No. 5,321,128), Woodward et al., (U.S. Pat. No. 5,093,329), Chan et al. (WO 92/08465) and Ueno et al. (EP 330 511 A$_2$) to reduce selectively or to eliminate altogether the side effects while maintaining the IOP-lowering effect. The Stjernschantz et al. publication is of particular interest because it reports that certain prostaglandin analogs, which retain the alicyclic rings characteristic of natural prostaglandins but which possess modifications in the omega chain, still exhibit the intraocular pressure lowering activity of the natural prostaglandins and have fewer adverse effects. These synthetic prostaglandins, like their natural counterparts, all possess the core, five-membered ring. Six-membered ring (cyclohexane) analogs of D, E and F series prostaglandins for lowering IOP are disclosed in commonly owned U.S. application Ser. Nos. 60/049,913 and 60/049,912.

Of interest in the present invention are compounds which are believed to exhibit IOP lowering mechanisms similar to those exhibited by natural D, E, and F series prostaglandins and their synthetic analogs while avoiding some or all of the undesirable side effects usually associated with the use of such compounds. An agent which exhibits comparable or improved efficacy, but with reduced side effects when compared to other gents, is said to have an improved therapeutic profile. It is an object of this invention to provide a novel class of IOP lowering agents with an improved therapeutic profile over the natural prostaglandins and many of their synthetic analogs. A further object of this invention is to provide methods of using the novel compounds in the treatment of glaucoma and ocular hypertension. It has now unexpectedly been discovered that the presently claimed cyclobutane analogs of PGD, PGE, and PGF meet this objective. Certain cyclobutane analogs of prostaglandins have been reported in the literature (see, Guzmán, et al., *Synthesis of Cyclobutano Prostaglandins, Chemistry and Industry,* 20:884–885 (1975); Greene et al., *Total Synthesis of 11-Nor Prostaglandins, Tetrahedron Letters,* 41:3755–3758 (1976); Reuschling et al., *Synthese von Cyclobutanprostaglandinen, Tetrahedron Letters,* 1:17–18 (1976); Depres et al., *Synthesis of Ring Modified Prostaglandins, Tetrahedron,* 37(3): 621–628 (1981); Reuschling et al. *Prostaglandin analog cyclobutane derivative,* (DE 2705675). The presently claimed compounds and methods, however, are neither disclosed nor suggested in the foregoing art.

SUMMARY OF THE INVENTION

The present invention is directed to novel compounds and compositions, and novel methods of using those compounds and other compounds in treating glaucoma and ocular hypertension. In particular, the present invention provides certain classes of analogs of the naturally occurring five-member ring prostaglandins, and methods of their use in treating glaucoma and ocular hypertension.

DETAILED DESCRIPTION OF THE INVENTION

It has unexpectedly been found that cyclobutane prostaglandin analogs of the present invention exhibit an improved therapeutic profile in the treatment of glaucoma and ocular hypertension when compared to natural (cyclopentane) prostaglandins and many of their known analogs. The cyclobutane prostaglandin analogs of the present invention have the following formula I:

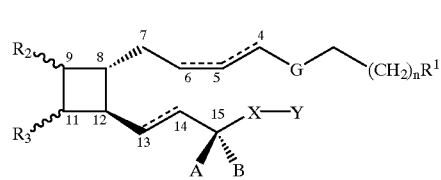

(I)

wherein:

R$^1$=CO$_2$R, CONR$^4$R$^5$, CH$_2$OR$^6$, or CH$_2$NR$^7$R$^8$; where:
R=H or cationic salt moiety, or CO$_2$R forms a pharmaceutically acceptable ester moiety;
R$^4$, R$^5$=same or different=H or alkyl;
R$^6$=H, acyl, or alkyl;
R$^7$, R$^8$=same or different=H, acyl, or alkyl; with the proviso that if one of R$^7$, R$^8$=acyl, then the other=H or alkyl;

n=0 or 2;

G=CH$_2$ or O;

R$^2$, R$^3$=same or different=H, OH, acyloxy, alkoxy, alkyl, carbonylalkoxy, carbonyl, or CH$_2$OR$^6$; with the proviso that at least one of R$^2$ or R$^3$=OH, acyl, alkoxy, carbonylalkoxy, carbonyl, CH$_2$OR$^6$; where R$^6$ is as defined above;

----=single or non-cumulated double bond;

one of A, B=H, the other=halo, OH, acyloxy, alkoxy;

X=(CH$_2$)$_q$ or (CH$_2$)$_q$O; where q=1–6; and

Y=a phenyl ring optionally substituted with alkyl, halo, trihalomethyl, alkoxy, acyl, acyloxy, amino, alkylamino, acylamino, or hydroxy; or X-Y=cyclohexyl, cyclopentyl, (CH$_2$)$_p$Y$^1$; where p=0–6; and $Y^1 =$ 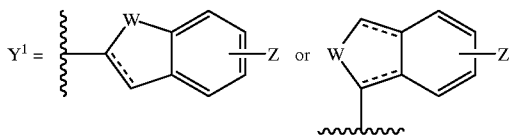

wherein:

W=$CH_2$, O, $S(O)_m$, $NR^9$, $CH_2CH_2$, CH=CH, $CH_2O$, $CH_2S(O)_m$, CH=N, or $CH_2NR^9$; where m=0–2, and $R^9$=H, alkyl, or acyl;

Z=H, alkyl, alkoxy, acyl, acyloxy, halo, trihalomethyl, amino, alkylamino, acylamino, or hydroxy; and ----=single or double bond.

As used herein, the term "pharmaceutically acceptable ester" means any ester that would be suitable for therapeutic administration to a patient by any conventional means without significant deleterious health consequences; and "ophthalmically acceptable ester" means any pharmaceutically acceptable ester that would be suitable for ophthalmic application, i.e. non-toxic and non-irritating. Wavy line attachments indicate that the configuration may be either alpha (α) or beta (β). The carbon numbering is as indicated in formula I, even when n=2. The dashed lines on bonds (e.g. between carbons 4 (C-4) and 5 (C-5), between carbons 5 (C-5) and 6 (C-6), and between carbons 13 (C-13) and 14 C-14)) indicate a single or double bond. Two solid lines present specify the configuration of the relevant double bond. Hatched lines indicate the a configuration. A solid triangular line indicates the β configuration.

The term "acyl" represents a group that is linked by a carbon atom that has a double bond to an oxygen atom and single bond to another carbon atom.

The term "acylamino" represents a group that is linked by an amino atom that is connected to a carbon atom has a double bond to an oxygen group and a single bond to a carbon atom or hydrogen atom.

The term "acyloxy" represents a group that is linked by an oxygen atom that is connected to a carbon that has a double bond to an oxygen atom and single bond to another carbon atom.

The term "alkenyl" includes straight or branched chain hydrocarbon groups having 1 to 15 carbon atoms with at least one carbon-carbon double bond. The chain hydrogens may be substituted with other groups, such as halogen. Preferred straight or branched alkeny groups include, allyl, 1-butenyl, 1-methyl-2-propenyl and 4-pentenyl.

The term "alkoxy" represents an alkyl group attached through an oxygen linkage.

The term "alkyl" includes straight or branched chain aliphatic hydrocarbon groups that are saturated and have 1 to 15 carbon atoms. The alkyl groups may be substituted with other groups, such as halogen, hydroxyl or alkoxy. Preferred straight or branched alkyl groups include methyl, ethyl, propyl, isopropyl, butyl and t-butyl.

The term "alkylamino" represents an alkyl group attached through a nitrogen linkage.

The term "alkynyl" includes straight or branched chain hydrocarbon groups having 1 to 15 carbon atoms with at least one carbon-carbon triple bond. The chain hydrogens may be substituted with other groups, such as halogen. Preferred straight or branched alkynyl groups include, 2-propynyl, 2-butynyl, 3-butynyl, 1-methyl-2-propynyl and 2-pentynyl.

The term "aryl" refers to carbon-based rings which are aromatic. Aromatic rings have alternating double and single bonds between an even number of atoms forming a system which is said to 'resonate'. The rings may be isolated, such as phenyl, or fused, such as naphthyl. The ring hydrogens may be substituted with other groups, such as lower alkyl, or halogen.

The term "carbonyl" represents a group that has a carbon atom that has a double bond to an oxygen atom.

The term "carbonylalkoxy" represents a group that is linked by a carbon atom that has a double bond to an oxygen atom and a single bond an alkoxy group.

The term "carbonyloxyl" represents a group that is linked by a carbon atom that has a double bond to an oxygen atom and a single bond a second oxygen atom.

The term "cycloalkyl" includes straight or branched chain, saturated or unsaturated aliphatic hydrocarbon groups which connect to form one or more rings, which can be fused or isolated. The rings may be substituted with other groups, such as halogen, hydroxyl or lower alkyl. Preferred cycloalkyl groups include cyclopropyl, cyclobutyl, cylopentyl and cyclohexyl.

The term "dialkylamino" represents two alkyl groups attached through a nitrogen linkage.

The term "halogen" represents fluoro, chloro, bromo, or iodo.

The term "heteroaryl" refers to aromatic hydrocarbon rings which contain at least one heteroatom such as O, S, or N in the ring. Heteroaryl rings may be isolated, with 5 to 6 ring atoms, or fused, with 8 to 10 atoms. The heteroaryl ring(s) hydrogens or heteroatoms with open valency may be substituted with other groups, such as lower alkyl or halogen. Examples of heteroaryl groups include imidazole, pyridine, indole, quinoline, furan, thiophene, pyrrole, tetrahydroquinoline, dihydrobenzofuran, and dihydrobenzindole.

The term "lower alkyl" represents alkyl groups containing one to six carbons ($C_1$–$C_6$).

Preferred compounds of the present invention are those of formula I above, wherein:

$R^1$=$CO_2R$, $CH_2OR^6$, where:
R=H; $R^6$ is as defined above, or $CO_2R$ forms a pharmaceutically acceptable ester moiety;
n=0;
G=$CH_2$;
$R^2$, $R^3$=same or different=H, OH, acyloxy, alkoxy, alkyl, carbonylalkoxy, carbonyl, or $CH_2OR^6$; with the proviso that at least one of $R^2$ or $R^3$=OH, acyl, alkoxy, carbonylalkoxy, carbonyl, $CH_2OR^6$; where $R^6$ is as defined above; and
B=OH or F.

Most preferred of the foregoing compounds are those of formula I wherein:

$R^1$=$CO_2R$, where R=H or $CO_2R$ forms a pharmaceutically acceptable ester moiety;
n=0;
G=$CH_2$;
$R^2$=H, OH, acyloxy, or $CH_2OR^6$; wherein $R^6$ is as defined above;
$R^3$=H, OH, or acyl;
B=OH;
X=$(CH_2)_q$ or $(CH_2)_qO$; where q=1 or 2
Y=a phenyl ring optionally substituted with alkyl, halo, trifluoromethyl, alkoxy, acyl, acyloxy, amino, alkylamino, acylamino, or hydroxy; or X-Y=(CH$_2$)$_p$Y$^1$; where p=0–2; and Y$^1$ is as defined above.

Other preferred compounds include those of formula I wherein:

R$^1$=CO$_2$R, CH$_2$OR$^6$, where: R=H; R$^6$ is as defined above; or CO$_2$R forms a pharmaceutically acceptable ester moiety;

n=0;

G=O;

R$^2$=H;

R$^3$=OH, acyl, CH$_2$OR$^6$ or carbonylalkoxy; where R$^6$ is as defined above;

One of A, B=OH; and

X-Y=cyclohexyl.

Examples of such most preferred compounds are the following:

| Compound Number | Compound Name | Compound Structure |
| --- | --- | --- |
| II | [1αR, 3Z, 2αS, 4βR, (1E, 3R)]-7-[2-hydroxy-4-[3-hydroxy-4-[3-(trifluoromethyl)phenoxy]-1-butenyl]cyclobutyl]-5-heptenoic acid isopropyl ester | 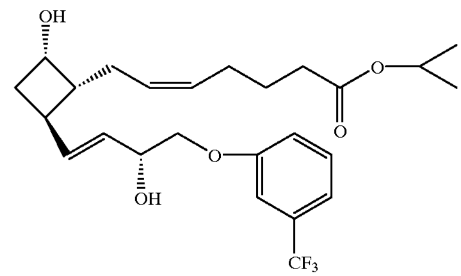 |
| III | [1αR, 3Z, 2αS, 4βR, (1E, 3R)]7-[2-hydroxymethyl-4-[3-hydroxy-4-[3-(trifluoromethyl)phenoxy]-1-butenyl]cyclobutyl]-5-heptenoic acid isopropyl ester | 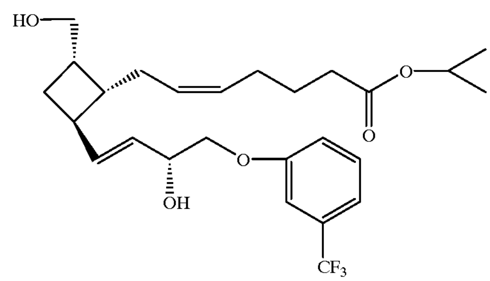 |
| IV | [1αR, 3Z, 2αS, 3αR, 4βR, (1E, 3R)]7-[3-hydroxy-2-hydroxymethyl-4-[3-hydroxy-4-[3-(trifluoromethyl)phenoxy]-1-butenyl]cyclobutyl]-5-heptenoic acid isopropyl ester | 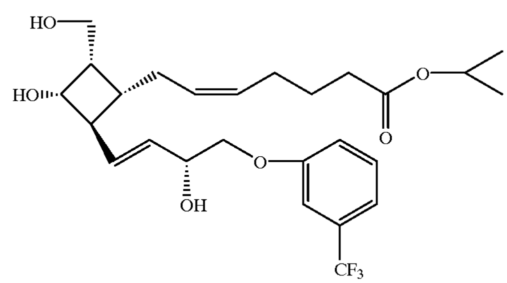 |
| V | [1αR, 3Z, 2αS, 4βR, (1E, 3R)]-7-[2-hydroxy-4-[3-hydroxy-4-[2-indanyl]-1-propenyl]cyclobutyl]-5-heptenoic acid isopropyl ester | 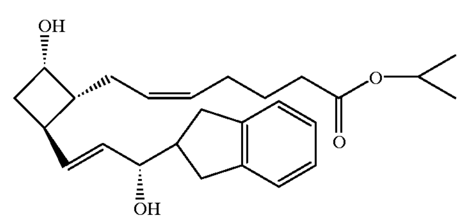 |
| VI | [1αR, 3Z, 2αS, 4βR, (1E, 3R)]-7-[2-hydroxymethyl-4-[3-hydroxy-4-[2-indanyl]-1-propenyl]cyclobutyl]-5-heptenoic acid isopropyl ester | 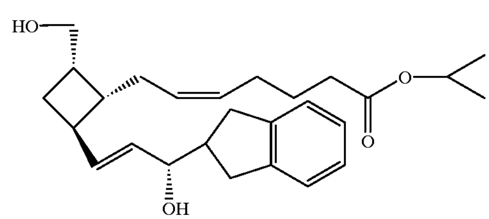 |

-continued

| Compound Number | Compound Name | Compound Structure |
|---|---|---|
| VII | [1αR, 3Z, 2αS, 4βR, (1E, 3R)]-7-[2-hydroxymethyl-4-[3-hydroxy-5-[phenyl]-1-pentenyl]cyclobutyl]-5-heptenoic acid isopropyl ester | 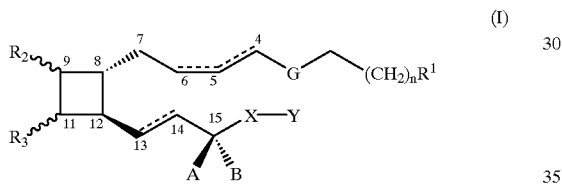 |
| VIII | [1αR, 3Z, 3αR, 4βR, (1E, 3R)]4-[3-hydroxy-4-[3-hydroxy-3-cyclohexyl]-1-propanyl]cyclobutyl]-2-butenoxy acetic acid isopropyl ester | 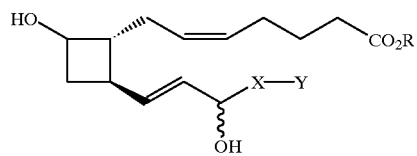 |

A number of compounds useful in the method of the present invention are believed to be novel. Those novel compounds are represented by formula I:

(I)

wherein:

$R^1=CO_2R$, $CONR^4R^5$, $CH_2OR^6$, or $CH_2NR^7R^8$; where:
  R=H or cationic salt moiety, or $CO_2R$ forms a pharmaceutically acceptable ester moiety;
  $R^4$, $R^5$=same or different=H or alkyl;
  $R^6$=H, acyl, or alkyl;
  $R^7$, $R^8$=same or different=H, acyl, or alkyl; with the proviso that if one of $R^7$, $R^8$=acyl, then the other=H or alkyl;

n=0 or 2;

G=$CH_2$ or O;

$R^2$, $R^3$=same or different=H, OH, acyloxy, alkoxy, alkyl, carbonylalkoxy, carbonyl, or $CH_2OR^6$; with the proviso that at least one of $R^2$ or $R^3$=OH, acyl, alkoxy, carbonylalkoxy, carbonyl, $CH_2OR^6$; where $R^6$ is as defined above;

----=single or non-cumulated double bond;

one of A, B=H, the other=halo, OH, acyloxy, alkoxy;

X=$(CH_2)_q$ or $(CH_2)_qO$; where q=1–6; and

Y=a phenyl ring optionally substituted with alkyl, halo, trihalomethyl, alkoxy, acyl, acyloxy, amino, alkylamino, acylamino, or hydroxy; or X-Y=cyclohexyl, cyclopentyl, $(CH_2)_pY^1$; where p=0–6; and $Y^1$ = 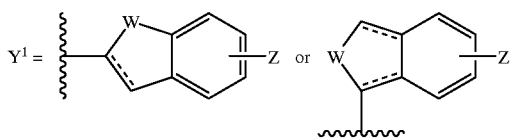

wherein:
  W=$CH_2$, O, $S(O)_m$, $NR^9$, $CH_2CH_2$, CH=CH, $CH_2O$, $CH_2S(O)_m$, CH=N, or $CH_2NR^9$; where m=0–2, and $R^9$=H, alkyl, or acyl;
  Z=H, alkyl, alkoxy, acyl, acyloxy, halo, trihalomethyl, amino, alkylamino, acylamino, or hydroxy; and
  ----=single or double bond;

with the proviso that the following compounds are excluded:

where R=H or cationic salt moiety, or $CO_2R$ forms a pharmaceutically acceptable ester;
X=$(CH_2)_q$ or $(CH_2)_qO$; where q=1–6; and
Y=a phenyl ring optionally substituted with alkyl, halo, trihalomethyl, alkoxy, acyl, acyloxy, amino, alkylamino, acylamino, or hydroxy.

Included within the scope of the present invention are the individual enantiomers of the title compounds, as well as their racemic and non-racemic mixtures. The individual enantiomers can be enantioselectively synthesized from the appropriate enantiomerically pure or enriched starting material following the procedure described below. Alternatively, they may be enantioselectively synthesized from racemic/non-racemic or achiral starting materials. (*Asymmetric Synthesis* by J. D. Morrison and J. W. Scott, Ed., Academic Press Publishers: New York, 1983–1985 (five volumes published over a three year span with chapters contributed by about two dozen authors) and *Principles of Asymmetric Synthesis* by R. E. Gawley and J. Aube, Ed., Elsevier Publishers: Amsterdam, 1996). They may also be isolated from racemic and non-racemic mixtures by a number of known methods, e.g. by purification of a sample by chiral HPLC (*A Practical Guide to Chiral Separations by HPLC*, G. Subramanian, Ed., VCH Publishers: New York, 1994; *Chiral Separations by HPLC*, A. M. Krstulovic, Ed., Ellis Horwood Ltd. Publishers, 1989), or by enantioselective hydrolysis of a carboxylic acid ester sample by an enzyme (Ohno, M.; Otsuka, M. *Organic Reactions*, volume 37, page 1 (1989)). Those skilled in the art will appreciate that racemic and non-racemic mixtures may be obtained by several means, including without limitation, nonenantioselective synthesis, partial resolution or even mixing samples having different enantiomeric ratios. Included within the scope of the present invention are the individual isomers of the disclosed compounds substantially free of their enantiomers.

In the following Examples 1–5, the following standard abbreviations are used: g=grams (mg=milligrams); mol= moles (mmol=millimoles); mL=milliliters; mm Hg=millimeters of mercury; mp=melting point; bp=boiling point; h=hours; and min=minutes. In addition, "NMR" refers to nuclear magnetic resonance spectroscopy and "MS" refers to mass spectrometry.

EXAMPLE 1

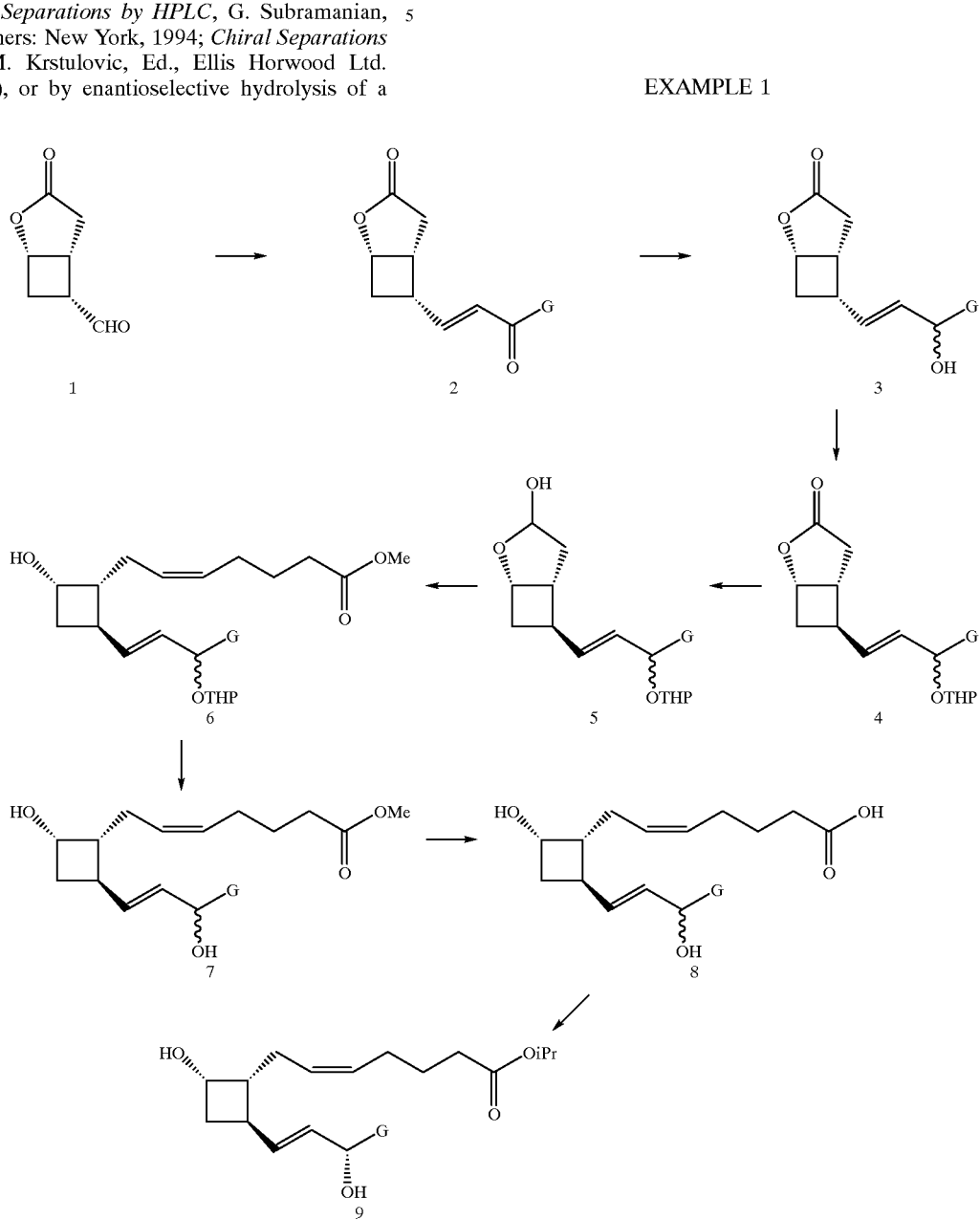

The cyclobutyl prostaglandin derivative (9) may be prepared from the aldehyde (1) by a multiple step procedure outlined in the foregoing schematic representation. Treatment of the aldehyde (1) with the sodium salt of the appropriate phosphonate followed by equilibration of the resulting enone using a base such as DBU provides the desired trans enone (2). Reduction of the enone with a reducing agent such as sodium borohyride or a mixture or cerium trichloride heptahydrate and sodium borohydride provides the enol (3). The enol can be protected as the THP ether (4) by adding dihydropyran to a solution of the alcohol and p-toluenesulfonic acid monohydrate in a solvent such as methylene chloride. The lactone (4) may be reduced to the hemiacetal (5) by treating with diisobutylaluminum hydride in a solvent such as tetrahydrofuran. The hemiacetal (5) may be reacted with the appropriate Wittig reagent generated from the substituted phosphonium bromide and a base such as dimsyl potassium or potassium tert-butoxide in a solvent such as tetrahydrofuran or dimethyl sulfoxide to form compound (6). Deprotection of the alcohol can be accomplished by treating the a solution of the THP ether (6) in a solvent mixture of methanol and water with hydrochloric acid. The resulting ester diol may be converted to the carboxylic acid by treating a solution of the methyl ester (7) with a base such as sodium hydroxide or lithium hydroxide in a solvent mixture of methanol and water. The carboxylic acid (8) may be converted to the isopropyl ester (9) by treating the compound with isopropyl iodide and a base such as DBU in a solvent such as acetone.

methods known to those skilled in the art (See, e.g., Reuschling, et al., *Synthese von Cyclobutanprostaglandinen*, Tetrahedron Letter 1: 17–18 (1976) and U.S. Pat. No. 3,772,350, the contents of which are by this reference incorproated herein).

The cyclobutyl prostaglandins of the present invention may be formulated in various pharmaceutical compositions for administering to humans and other mammals as a treatment of glaucoma or ocular hypertension. As used herein, the term "pharmaceutically effective amount" refers to that amount of a compound of the present invention which lowers IOP when administered to a patient, especially a mammal. The preferred route of administration is topical. The compounds of the present invention can be administered as solutions, suspensions, or emulsions (dispersions) in an ophthalmically acceptable vehicle. As used herein, the term "ophthalmically acceptable vehicle" refers to any substance or combination of substances which are non-reactive with

EXAMPLE 2

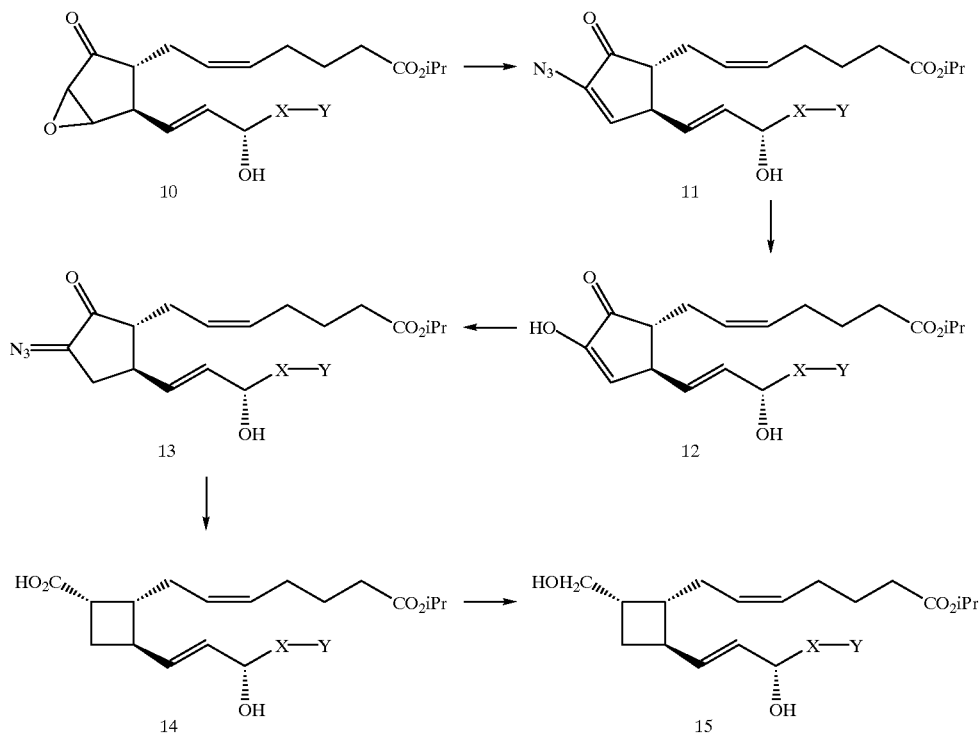

The cyclobutyl prostaglandin derivative (15) may be prepared from the epoxide (10) by a multiple step procedure outlined in the foregoing schematic representation. The azido ketone (11) may be prepared by reacting the epoxide (10) with sodium azide in a methanol-water-dioxane. Conversion of (11) to the enolic α-diketone (12) may be brought about by the treatment of the azido ketone (11) with ammonium sulfide in a solvent such as methanol. The enolic α-diketone (12) can be converted into the α-diazoketone (13) by warming a methanolic solution of (12) and toluene-p-sulfonylhydrazine. The α-diazoketone (13) may be converted to the cyclobutyl derivative (14) by photolysis in a solvent system comprised of methanol and water. The carboxylic acid (14) may be converted to the ester (15) by the sodium hydride mediated reduction of the mixed anhydride formed by reacting ethyl chloroformate with the carboxylic acid (14).

The starting materials (1) and (10) described in Examples 1 and 2, respectively, can be prepared by conventional the compounds and suitable for administration to a patient. Solubilizers and stabilizers are deemed to be non-reactive. Preferred are aqueous vehicles suitable for topical application to the patient's eyes.

In forming compositions for topical administration, the compounds of the present invention are generally formulated as between about 0.00003 to about 0.5 percent by weight (wt %) solutions in water at a pH between 4.5 to 8.0, preferably between about 7.0 and 7.5. The compounds are preferably formulated as between about 0.0005 to about 0.03 wt % and, most preferably, between about 0.001 and about 0.01 wt %. While the precise regimen is left to the discretion of the clinician, it is recommended that the resulting solution be topically applied by placing one drop in each eye one or two times a day.

Other ingredients which may be desirable to use in the ophthalmic preparations of the present invention include preservatives, co-solvents, and viscosity building agents.

Antimicrobial Preservatives:

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M, or other agents known to those skilled in the art. Such preservatives are typically employed at a level between about 0.001% and about 1.0% by weight.

Co-Solvents

Prostaglandins, and particularly ester derivatives, typically have limited solubility in water and therefore may require a surfactant or other appropriate co-solvent in the composition. Such co-solvents include: Polysorbate 20, 60 and 80; Pluronic F-68, F-84 and P-103; CREMOPHORE® EL (polyoxyl 35 castor oil); cyclodextrin; or other agents known to those skilled in the art. Such co-solvents are typically employed at a level between about 0.01% and about 2% by weight.

Viscosity Agents

Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxy propyl methyl cellulose, hydroxyethyl cellulose, carboxymethyl cellulose, hydroxy propyl cellulose, chondroitin sulfate and salts thereof, hyaluronic acid and salts thereof, and other agents known to those skilled in the art. Such agents are typically employed at a level between about 0.01% and about 2% by weight.

Preferred formulations of the cyclobutyl prostaglandins of the present invention include the following Examples 2–4:

EXAMPLE 2

| Ingredient | Amount (wt %) |
|---|---|
| Compound III | 0.01 |
| Phosphate Buffered Saline | 1.0 |
| Polysorbate 80 | 0.5 |
| Purified water | q.s. to 100% |

EXAMPLE 3

| Ingredient | Amount (wt %) |
|---|---|
| Compound V | 0.005 |
| Monobasic sodium phosphate | 0.05 |
| Dibasic sodium phosphate (anhydrous) | 0.15 |
| Sodium chloride | 0.75 |
| Disodium EDTA (Edetate disodium) | 0.05 |
| CREMOPHOR ® EL | 0.1 |
| Benzalkonium chloride | 0.01 |
| HCl and/or NaOH | pH 7.3–7.4 |
| Purified water | q.s. to 100% |

EXAMPLE 4

| Ingredient | Amount (wt %) |
|---|---|
| Compound II | 0.1 |
| Phosphate Buffered Saline | 1.0 |
| Hydroxypropyl-β-cyclodextrin | 4.0 |
| Purified water | q.s. to 100% |

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A method of treating glaucoma and ocular hypertension which comprises administering to an effected eye an intraocular pressure lowering effective amount of a compound of formula I:

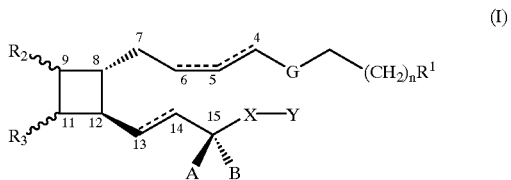

wherein:

$R^1$=$CO_2R$, $CONR^4R^5$, $CH_2OR^6$, or $CH_2NR^7R^8$; where:
  R=H or cationic salt moiety, or $CO_2R$ forms a pharmaceutically acceptable ester moiety;
  $R^4$, $R^5$=same or different=H or alkyl;
  $R^6$=H, acyl, or alkyl;
  $R^7$, $R^8$=same or different=H, acyl, or alkyl; with the proviso that if one of $R^7$, $R^8$=acyl, then the other=H or alkyl;

n=0 or 2;

G=$CH_2$ or O;

$R^2$, $R^3$=same or different=H, OH, ocyloxy, alkoxy, alkyl, carbonylalkoxy, carbonyl, or $CH_2OR^6$; with the proviso that at least one of $R^2$ or $R^3$=OH, acyl, alkoxy, carbonylalkoxy, carbonyl, $CH_2OR^6$; where $R^6$ is as defined above;

----=single or non-cumulated double bond;

one of A, B=H, the other=halo, OH, acyloxy, alkoxy;

X=$(CH_2)_q$ or $(CH_2)_qO$; where q=1–6; and

Y=a phenyl ring optionally substituted with alkyl, halo, trihalomethyl, alkoxy, acyl, acyloxy, amino, alkylamino, acylamino, or hydroxy; or X-Y=cyclohexyl, cyclopentyl, $(CH_2)_pY^1$; where p=0–6; and

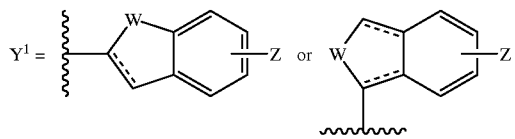

wherein:
W=CH$_2$, O, S(O)$_m$, NR$^9$, CH$_2$CH$_2$, CH=CH, CH$_2$O, CH$_2$S(O)$_m$, CH=N, or CH$_2$NR$^9$; where m=0–2, and R$^9$=H, alkyl, or acyl;

Z=H, alkyl, alkoxy, acyl, acyloxy, halo, trihalomethyl, amino, alkylamino, acylamino, or hydroxy; and ----=single or double bond.

2. The method of claim 1, wherein the compound is administered topically.

3. The method of claim 2, wherein the compound is administered as a solution, suspension, or emulsion in an ophthalmically acceptable vehicle.

4. The method of claim 2, wherein the concentration of the compound is between about 0.00003 to about 0.5 weight percent.

5. The method of claim 4, wherein the concentration of the compound is between about 0.0005 to about 0.03 weight percent.

6. The method of claim 5, wherein the concentration of the compound is between about 0.001 to about 0.01 weight percent.

7. The method of claim 1, wherein the compound is:

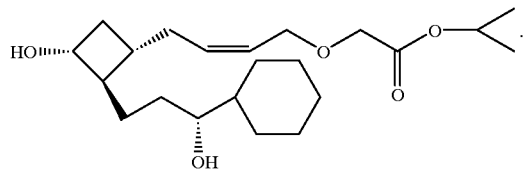

8. The method of claim 1, wherein for the compound of formula I:
R$^1$=CO$_2$R, CH$_2$OR$^6$, where:
R=H; R$^6$=H, acyl, or alkyl; or CO$_2$R forms a pharmaceutically acceptable ester moiety;
n=0;
G=CH$_2$;
R$^2$, R$^3$=same or different=H, OH, acyloxy, alkoxy, alkyl, carbonylalkoxy, carbonyl, or CH$_2$OR$^6$; with the proviso that at least one of R$^2$ or R$^3$=OH, acyl, alkoxy, carbonylalkoxy, carbonyl, or CH$_2$OR$^6$; where R$^6$ is as defined above; and
B=OH or F.

9. The method of claim 8, wherein for the compound of formula I:
R$^1$=CO$_2$R, where R=H or CO$_2$R forms a pharmaceutically acceptable ester moiety;
n=0;
G=CH$_2$;
R$^2$=H, OH, acyloxy, or CH$_2$OR$^6$; wherein R$^6$=H, acyl, or alkyl;
R$^3$=H, OH, or acyl; with the proviso that at least one of R$_2$ or R$_3$=OH, acyl, acyloxy, or CH$_2$OR$^6$; where R$^6$ is as defined above.

B=OH;
X=(CH$_2$)$_q$ or (CH$_2$)$_q$O; where q=1 or 2
Y=a phenyl ring optionally substituted with alkyl, halo, trifluoromethyl, alkoxy, acyl, acyloxy, amino, alkylamino, acylamino, or hydroxy; or
X-Y=(CH$_2$)$_p$Y$^1$; where p=0–2; and Y$^1$ is as defined above.

10. The method of claim 9, wherein the compound is:

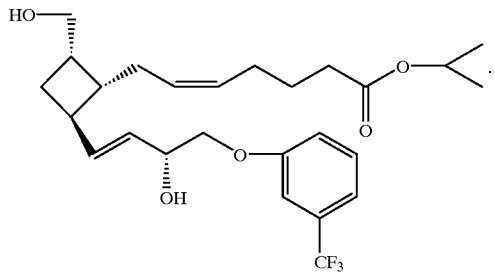

11. The method of claim 9, wherein the compound is:

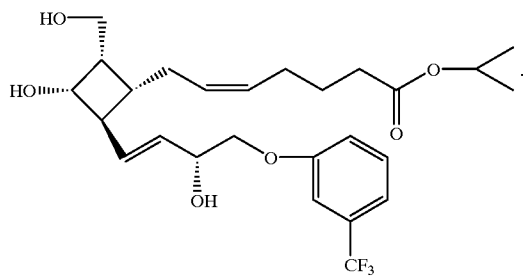

12. The method of claim 9, wherein the compound is:

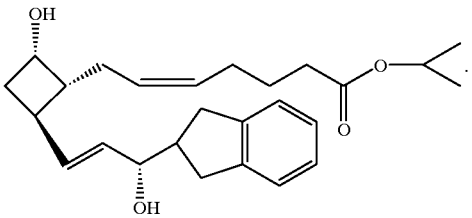

13. The method of claim 9, wherein the compound is:

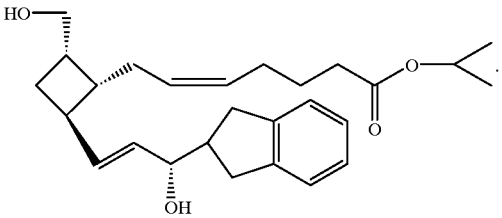

14. The method of claim 9, wherein the compound is:

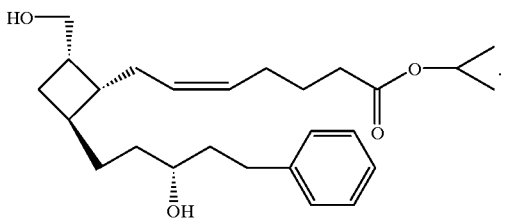

15. A compound of formula I:

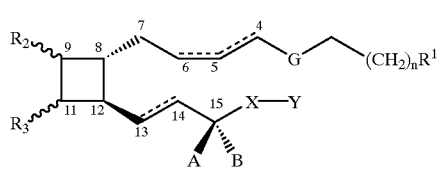

(I)

wherein:

$R^1$=$CO_2R$, $CONR^4R^5$, $CH_2OR^6$, or $CH_2NR^7R^8$; where:
R=H or cationic salt moiety, or $CO_2R$ forms a pharmaceutically acceptable ester moiety;
$R^4$, $R^5$=same or different=H or alkyl;
$R^6$=H, acyl, or alkyl;
$R^7$, $R^8$=same or different=H, acyl, or alkyl; with the proviso that if one of $R^7$, $R^8$=acyl, then the other=H or alkyl;
n=0 or 2;
G=$CH_2$ or O;
$R^2$=H, alkyl, carbonylalkoxy, carbonyl, or $CH_2OR^6$; where $R^6$ is as defined above;
$R^3$=H, OH, acyloxy, alkoxy, alkyl, carbonylalkoxy, carbonyl, or $CH_2OR^6$; where $R^6$ is as defined above;
with the proviso that when one of $R^2$, $R^3$=H or alkyl, then the other cannot be H or alkyl;
----=single or non-cumulated double bond;
one of A, B=H, the other=halo, OH, acyloxy, alkoxy;
X=$(CH_2)_q$ or $(CH_2)_qO$; where q=1–6; and
Y=a phenyl ring optionally substituted with alkyl, halo, trihalomethyl, alkoxy, acyl, acyloxy, amino, alkylamino, acylamino, or hydroxy; or
X-Y=cyclohexyl, cyclopentyl, $(CH_2)_pY^1$; where p=0–6; and

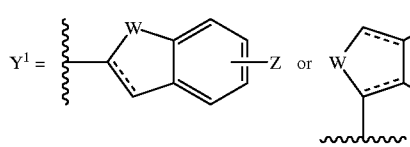

wherein:
W=$CH_2$, O, $S(O)_m$, $NR^9$, $CH_2CH_2$, CH=CH, $CH_2O$, $CH_2S(O)_m$, CH=N, or $CH_2NR^9$; where m=0–2, and $R^9$=H, alkyl, or acyl;
Z=H, alkyl, alkoxy, acyl, acyloxy, halo, trihalomethyl, amino, alkylamino, acylamino, or hydroxy; and
----=single or double bond.

16. The compound of claim 15, having the formula:

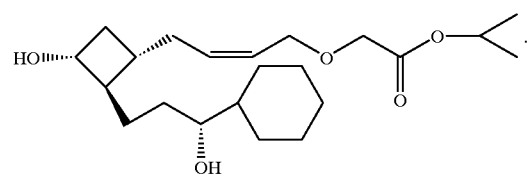

17. The compound of claim 15, wherein for the compound of formula I:

$R^1$=$CO_2R$, $CH_2OR^6$, where:
R=H; $R^6$=H, acyl, or alkyl; or $CO_2R$ forms a pharmaceutically acceptable ester moiety;
n=0;
G=$CH_2$;
$R^2$=H, alkyl, carbonylalkoxy, carbonyl, or $CH_2OR^6$; where $R^6$=H, acyl, or alkyl;
$R^3$=H, OH, acyloxy, alkoxy, alkyl, carbonylalky, carbonyl, or $CH_2OR^6$; where $R^6$=H, acyl, or alkyl;
with the proviso that when one of $R^2$, $R^3$=H or alkyl, then the other cannot be H or alkyl; and
B=OH or F.

18. The compound of claim 17, having the formula:

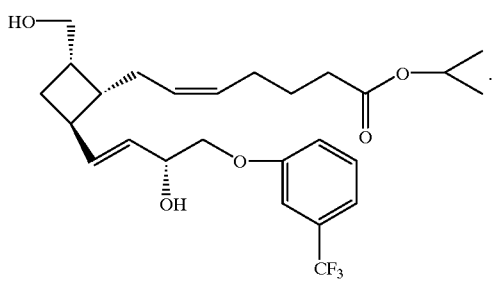

19. The compound of claim 17, having the formula:

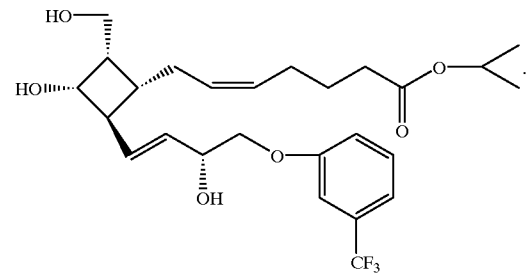

20. The compound of claim 17, having the formula:

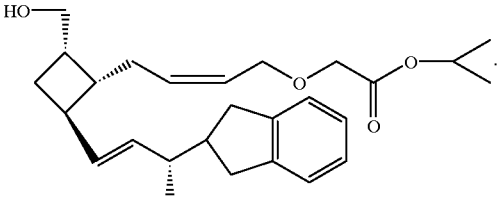

21. The compound of claim 17, having the formula:

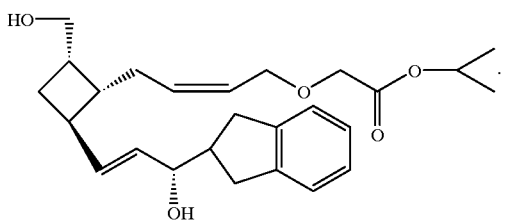

22. The compound of claim 17, having the formula:

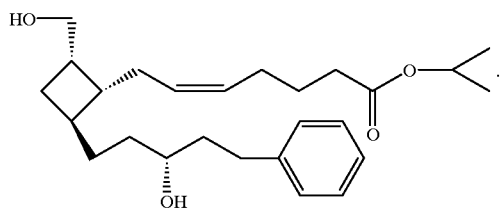

23. An ophthalmic composition for the treatment of glaucoma and ocular hypertension, comprising a compound of formula I:

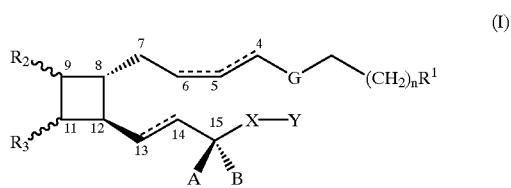

wherein:
$R^1$=$CO_2R$, $CONR^4R^5$, $CH_2OR^6$, or $CH_2NR^7R^8$; where:
R=H or cationic salt moiety, or $CO_2R$ forms a pharmaceutically acceptable ester moiety;
$R^4$, $R^5$=same or different=H or alkyl;
$R^6$=H, acyl, or alkyl;
$R^7$, $R^8$=same or different=H, acyl, or alkyl; with the proviso that if one of $R^7$, $R^8$=acyl, then the other=H or alkyl;
n=0 or 2;
G=$CH_2$ or O;
$R^2$, $R^3$=same or different=H, OH, acyloxy, alkoxy, alkyl, carbonylalkoxy, carbonyl, or $CH_2OR^6$; with the proviso that at least one of $R^2$ or $R^3$=OH, acyl, alkoxy, carbonylalkoxy, carbonyl, $CH_2OR^6$; where $R^6$ is as defined above;
----=single or non-cumulated double bond;
one of A, B=H, the other=halo, OH, acyloxy, or alkoxy;
X=$(CH_2)_q$ or $(CH_2)_qO$; where q=1–6; and
Y=a phenyl ring optionally substituted with alkyl, halo, trihalomethyl, alkoxy, acyl, acyloxy, amino, alkylamino, acylamino, or hydroxy; or
X-Y=cyclohexyl, cyclopentyl, or $(CH_2)_pY^1$; where p=0–6; and

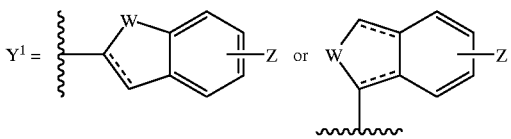

wherein:
W=$CH_2$, O, $S(O)_m$, $NR^9$, $CH_2CH_2$, CH=CH, $CH_2O$, $CH_2S(O)_m$, CH=N, or $CH_2NR^9$; where m=0–2, and $R^9$=H, alkyl, or acyl;
Z=H, alkyl, alkoxy, acyl, acyloxy, halo, trihalomethyl, amino, alkylamino, acylamino, or hydroxy;
----=single or double bond; and
an ophthalmically acceptable vehicle therefor.

24. The composition of claim 18, wherein for the compound of formula I:
$R^1$=$CO_2R$, $CH_2OR^6$, where:
R=H; $R^6$=H, acyl, or alkyl; or $CO_2R$ forms a pharmaceutically acceptable ester moiety;
n=0;
G=$CH_2$;
$R^2$, $R^3$=same or different=H, OH, acyloxy, alkoxy, alkyl, carbonylalkoxy, carbonyl, or $CH_2OR^6$; with the proviso that at least one of $R^2R^3$=OH, acyl, alkoxy, carbonylalkoxy, carbonyl, $CH_2OR^6$; where $R^6$=H, acyl, or alkyl; and
B=OH or F.

25. The composition of claim 24, wherein the compound has the following formula:

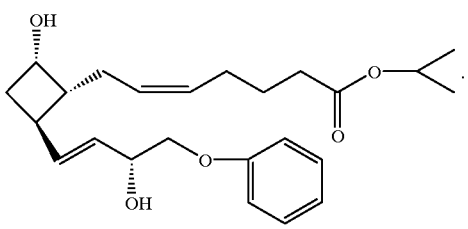

* * * * *